(12) United States Patent
Olivier et al.

(10) Patent No.: US 7,273,750 B1
(45) Date of Patent: Sep. 25, 2007

(54) BIOLOGICAL CULTURE GROWTH AND OBSERVATION DEVICE

(75) Inventors: Stéphane Olivier, Strasbourg (FR); Gérard Muller, Urmatt (FR)

(73) Assignee: Millipore Corporation, Billerica, MA (US)

( * ) Notice: Subject to any disclaimer, the term of this patent is extended or adjusted under 35 U.S.C. 154(b) by 0 days.

(21) Appl. No.: 10/182,279

(22) PCT Filed: Jan. 31, 2000

(86) PCT No.: PCT/EP00/01100

§ 371 (c)(1),
(2), (4) Date: Oct. 3, 2002

(87) PCT Pub. No.: WO01/57178

PCT Pub. Date: Aug. 9, 2001

(51) Int. Cl.
*C12M 1/22* (2006.01)
*B65D 51/20* (2006.01)
*B65D 43/04* (2006.01)

(52) U.S. Cl. .............................. 435/288.4; 435/288.5; 435/305.3; 435/305.4; 422/102; 220/257.1; 220/257.2; 220/281

(58) Field of Classification Search ............. 435/305.4, 435/305.3; 220/257.1, 787, 789, 791, 281
See application file for complete search history.

(56) References Cited

U.S. PATENT DOCUMENTS

| | | | | |
|---|---|---|---|---|
| 3,552,634 A | * | 1/1971 | Ollier et al. ............. | 229/123.1 |
| 3,561,668 A | * | 2/1971 | Bergstrom ................ | 229/123.1 |
| 4,413,748 A | * | 11/1983 | Kessler et al. .............. | 220/281 |
| 4,668,633 A | | 5/1987 | Walton ........................ | 435/298 |
| 4,721,679 A | | 1/1988 | Yiu et al. .................... | 435/301 |
| 6,261,523 B1 | * | 7/2001 | Schembri ..................... | 422/102 |

FOREIGN PATENT DOCUMENTS

| | | |
|---|---|---|
| DE | 24 33 055 | 1/1976 |
| DE | 32 18 532 | 11/1983 |
| EP | 0 149 383 | 7/1985 |
| EP | 0 866 122 | 9/1998 |
| FR | 1 572 527 | 6/1969 |
| FR | 2 486 915 | 1/1982 |
| FR | 2 617 500 | 1/1989 |

* cited by examiner

*Primary Examiner*—William H Beisner
(74) *Attorney, Agent, or Firm*—Nields & Lemack

(57) ABSTRACT

The present invention provides a biological culture growth and observation device (1) comprising a cup-shaped tray (2) for containing or receiving a growth medium for said biological culture and a cap (4) which matches said tray (2) and which can be snapped on and off said tray (2), characterized in that said cap (4) and tray (2) are provided with means (5) to snap on/off said cap (4) on/off the inner walls (6) of said tray (2) and in that said cup-shaped tray (2) is realized with walls (7) having a first circumferential edge (8) on which a removable seal (10) can be fixed to cover the surface of said edge (8) and the cap (4) snapped on the tray (2) before the first use of the device (1).

18 Claims, 6 Drawing Sheets

Fig-6

BIOLOGICAL CULTURE GROWTH AND OBSERVATION DEVICE

This invention relates to the field of biology or microbiology and more particularly to a biological culture growth, observation and identification device. The present invention provides an improved biological culture growth, observation and identification device for manipulating, growing, storing, transporting, observing and identifying living organisms like biological cultures, human or animal cells, vegetal cells, bacteria, yeasts, fungi, microbiological material and the like.

Currently, biological or microbiological material or the like is handled in well known so-called <<Petri-dishes >>, consisting generally of flat cylindrical glass- or plastic dishes topped by circular glass or plastic plates or covers which rest loosely on the said dishes. This wide-spread construction is very simple and thus very cheap to manufacture. Nevertheless, it has several, some of them important, drawbacks.

For instance, the cover is not designed to be tightly fixed to the dish and can always rotate (circular dishes) and/or fall down thereby being contaminated or even broken. Also because of the circular section of Petri-dishes the fixing of the covers may represent a big problem. Although the fixing of said covers with rubberbands may be a solution for small numbers of dishes, this option quickly becomes a tedious task when the number of dishes increases, for example in a laboratory.

Fixing Petri-dish covers with adhesive tape leaves traces on the dishes which may obstruct observation and tend to make the dishes become sticky thereby increasing the risk of contamination or destruction.

Moreover, the side-walls and especially the top cover tend to cover with condensation because of the moisture that is contained in the dishes or because of the growing of the living organisms placed in there, making therefore any clear observation difficult or impossible.

The handling, particularly with gloved hands, of the aformentioned glass dishes may also become dangerous as said glass dishes tend to be or to become very slippery when getting wet.

Other known devices permit the growth, transportation and observation of biological structures while minimizing damage to the biological structure. They perform the functions of culture growth, transportation and identification in one single device.

For instance, U.S. Pat. No. 5,661,029 discloses a biological culture growth and observation system that includes a tray with a resealable top. This tray further includes a depression or well to contain a growth medium in which to grow an organism. This system can also include a separate barrier layer sealed over the medium well.

When being used, the lid is peeled back, the barrier layer removed and a biological sample introduced onto the growth medium. The lid is then resealed in the original position to enable the growing and observation of the growing a different stages.

Nevertheless, because of the resealable lid, contamination may occur, especially on the parts of the lid on which adhesive material is deposited, thereby also affecting the adhesive properties of said material.

In addition to the above mentioned problems, the above quoted prior art device always needs to be manipulated with both hands of the operator (one to hold the not entirely back-peeled resealable lid while the other hand is removing the barrier and depositing the organisms) so that supplemental contamination may occur. Besides, this known device is not stackable and needs more space to be stored, transported or when being thrown away or destroyed.

The present invention consists of a polyvalent improved device to conduct biological or microbiological growing, observation and/or identification in the same device, which avoids at least some of the above mentioned drawbacks and which presents some new and innovative features to improve the general using or handling conditions of said device. It also provides a device that can be stacked and thus easily transported, stored or disposed after its use without being too complicated or too expensive to manufacture in comparison to its competitors.

The biological culture growth and observation device of the present invention is comprising a cup-shaped tray for containing or receiving a growth medium for said biological culture and a cap which matches said tray and which can be snapped on and off said tray, characterized in that said cap and tray are provided with means to snap on/off said cap on/off the inner walls of said tray and in that said cup-shaped tray is realized with walls having a first circumferential edge on which a removable seal can be fixed to cover the surface of said edge said cap snapped on said tray before the first use of the device.

The above gives a broad description of the present invention one non limitative preferred form of which will now be described with reference to the accompanying drawings in which.

Figures 1, 1A:
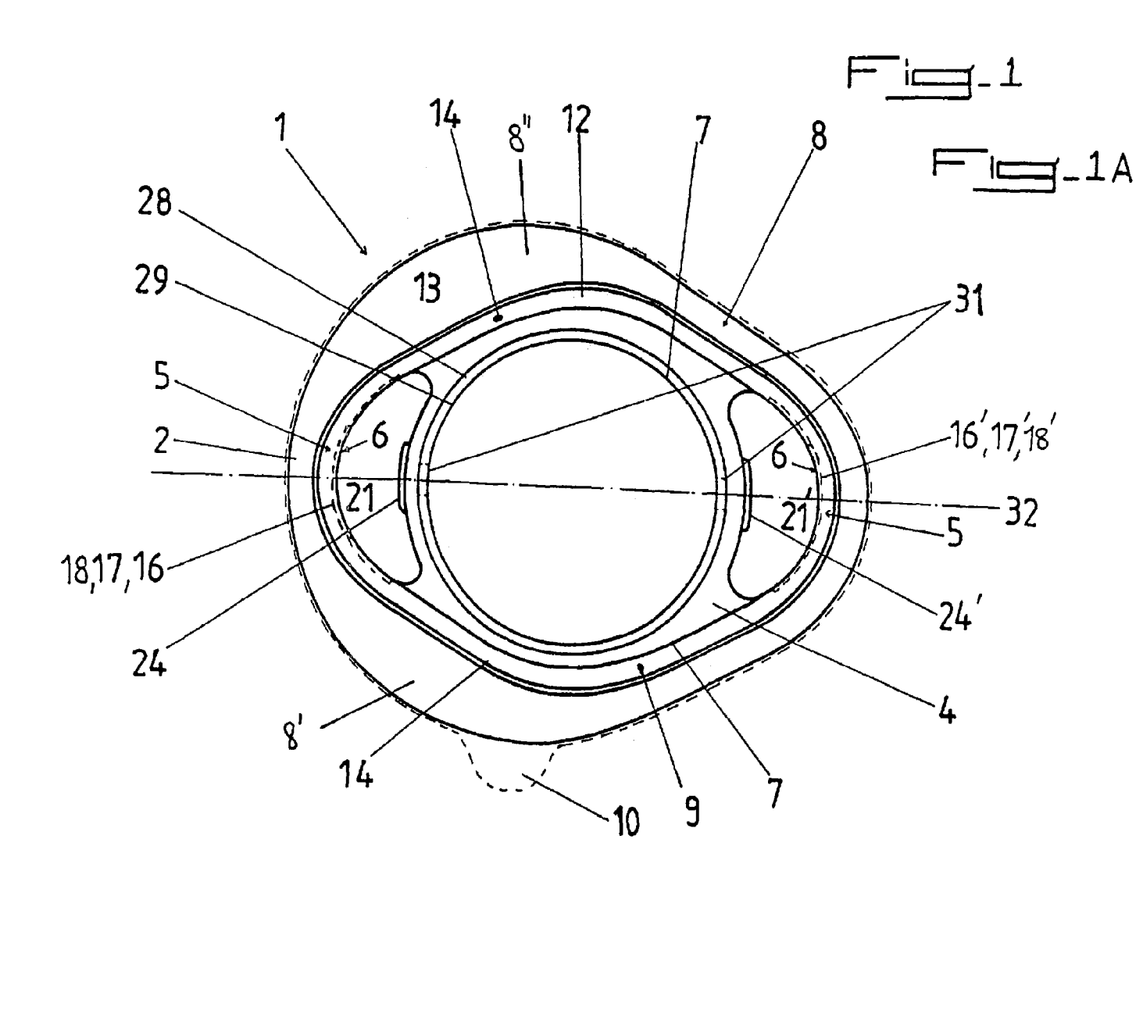
FIG. 1A is a top view of a complete biological culture growth and observation device (tray, cap and seal) according to the present invention.

The FIG. 1A of FIG. 1, shows a top view of a complete biological culture growth and observation device 1 according to the present invention.

Referring to FIG. 1A, a complete device 1 is comprising a cup-shaped tray 2 for containing or receiving a growth medium 3 for a biological culture B (shown on FIG. 1B) and a cap 4 which matches said tray 2 and which can be snapped on and off said tray 2, characterized in that said cap 4 and tray 2 are provided with means 5 to snap on/off said cap 4 on/off the inner walls 6 of said tray 2 and in that said cup-shaped tray 2 is realized with walls 7 having a first circumferential edge 8 on which a removable seal 10 can be fixed to cover the surface of said first edge 8 and said cap 4 which is snapped on said tray 2 before the first use of the device 1.

According to a preferred embodiment, the device 1 of the present invention is characterized in that the first circumferential edge 8 of the walls 7 of said cup-shaped tray 2 is extending outwards the inner volume 11 defined by said tray 2.

Figure 4:
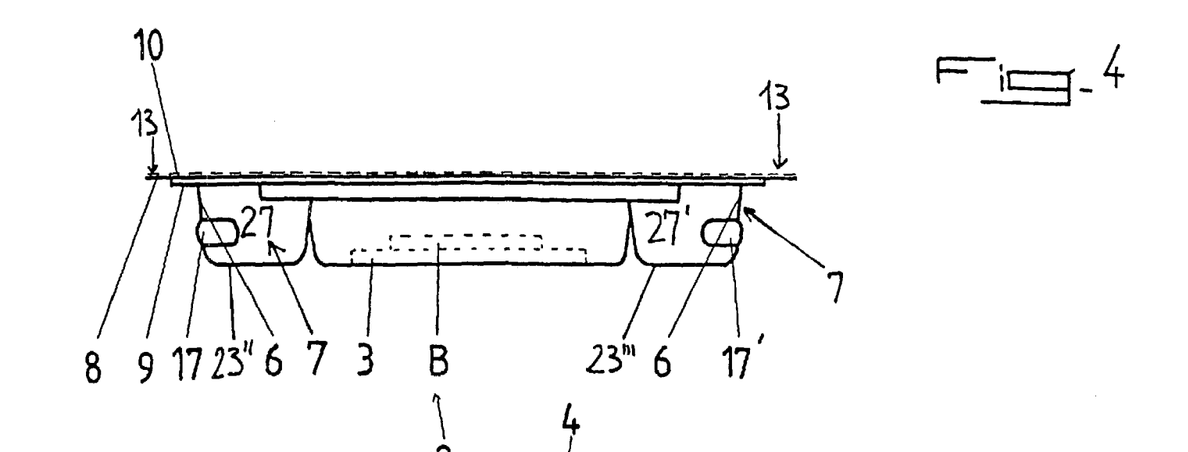
FIG. 4 is a lateral view of the tray of a biological culture growth and observation device according to the present invention.

As seen on FIG. 1A in connection with FIG. 4, the device 1 according to this embodiment is characterized in that the cup-shaped tray 2 is realized with walls 7 having a second circumferential outwardly extending edge 9 at a lower level than the level of the first circumferential outwardly extending edge 8 and in that the cap 4 has a corresponding circumferential outwardly extending edge 12 which is aligned with said second circumferential outwardly extending edge 9 when said cap 4 is snapped on said tray 2.

Preferably and as shown in the illustrated example, the first surface 13 of the first circumferential outwardly extending edge 8 of the cup-shaped tray 2 and the second surface 14 of the corresponding edge 12 of the cap 4 snapped on said tray 2 are in the same plane or nearly the same plane at nearly the same level.

Advantageously, the device 1 according to the present invention has the surface 15 of the cap 4 realized as a plane or nearly plane surface. This allows for the complete devices 1 to be stored in a minimum space before their first use (see FIGS. 5 and 6).

As illustrated on FIG. 1A, the device 1 is also characterized in that said cap 4 is snapped on/off the inner wall(s) 6 of said tray 2 by means of at least one locking unit 16, 16'.

Figure 5:
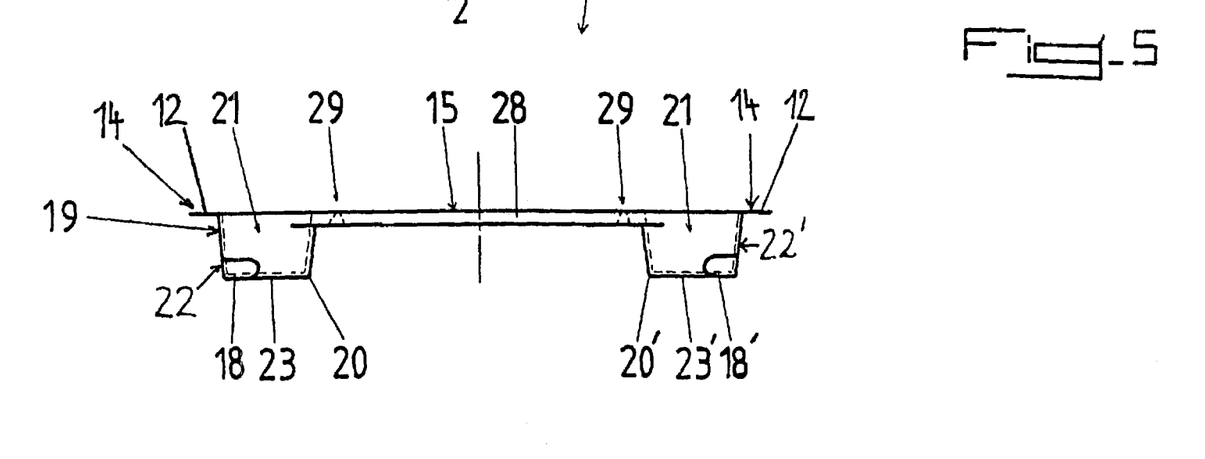
FIG. 5 is a lateral view of the cap corresponding to the tray of FIG. 4.

Each of these locking units 16, 16' is consisting of a first element 17 located on the inner wall(s) 6 of said tray 2 which is collaborating with at least one second element 18 located on at least one outer surface 19 of at least one locking member 20, 20' extending in a perpendicularly or nearly perpendicularly direction out of the surface 15 covered by said cap 4 near the outer periphery of said cap 4 said first 17 and second 18 elements having complementary engaging surfaces 17', 18' which cooperate together to allow the cap 4 to be snapped on/off the cup-shaped tray 2 (see FIGS. 4 and 5).

In the preferred embodiment represented on FIGS. 4 and 5, the first element 17 and second element 18 of each locking unit 16, 16' consist of a rib/groove collaborating with a corresponding groove/rib having a complementary shape.

Of course, all other complementary male-female forms can be used to realize the first element 17 and second, with first element 17 collaborating, element 18 of the locking units 16, 16'.

Advantageously and as seen in the version represented for instance on FIG. 1A, the device 1 presents two locking units 16, 16' being placed on opposite areas of tray 2 and cap 4 to maximize the distance between said locking units 16, 16'.

Referring especially to FIGS. 1A and 5, device 1 according to the invention is having a cap 4 which presents at least one cavity or recess 21, 21' formed in the covering surface 15 of said cap 4 to receive manipulating human fingers or instruments to hold, move, lay down and snap on/off the said cap 4 on the cup-shaped tray 2.

Thanks to these cavities or recesses 21, 21', the device 1 according to the present invention can be easily opened with only one hand and without being compelled to hold the tray 2 with the other hand, the last being able to execute any operation on the tray 2, especially on the growth medium 3, without laying down the cap 4 thus avoiding supplemental risks of contamination of said cap 4.

As a consequence, the device 1 may be characterized in that the cap 4 presents two in-molded or in-formed cavities or recesses 21, 21' on the covering surface 15 of said cap 4 in such a way that one cavity or recess 21, 21' may receive the thumb of a user's hand whereas the other cavity or recess 21, 21' may receive the index finger and/or another finger of the same hand, thereby allowing said cap 4 to be snapped on/off said tray 2 with only one hand thanks to the locking units 16, 16' placed at said cavities or recesses 21, 21', the snapping-off consisting in the disengaging of the complementary shaped first and second elements 17, 18 of the locking units 16, 16', said disengaging being realized by a flexion of the cap 4 and the cup-shaped tray 2, said flexion moving said first and second elements 17, 18 of said locking units 16, 16' away from each other.

Figure 3:
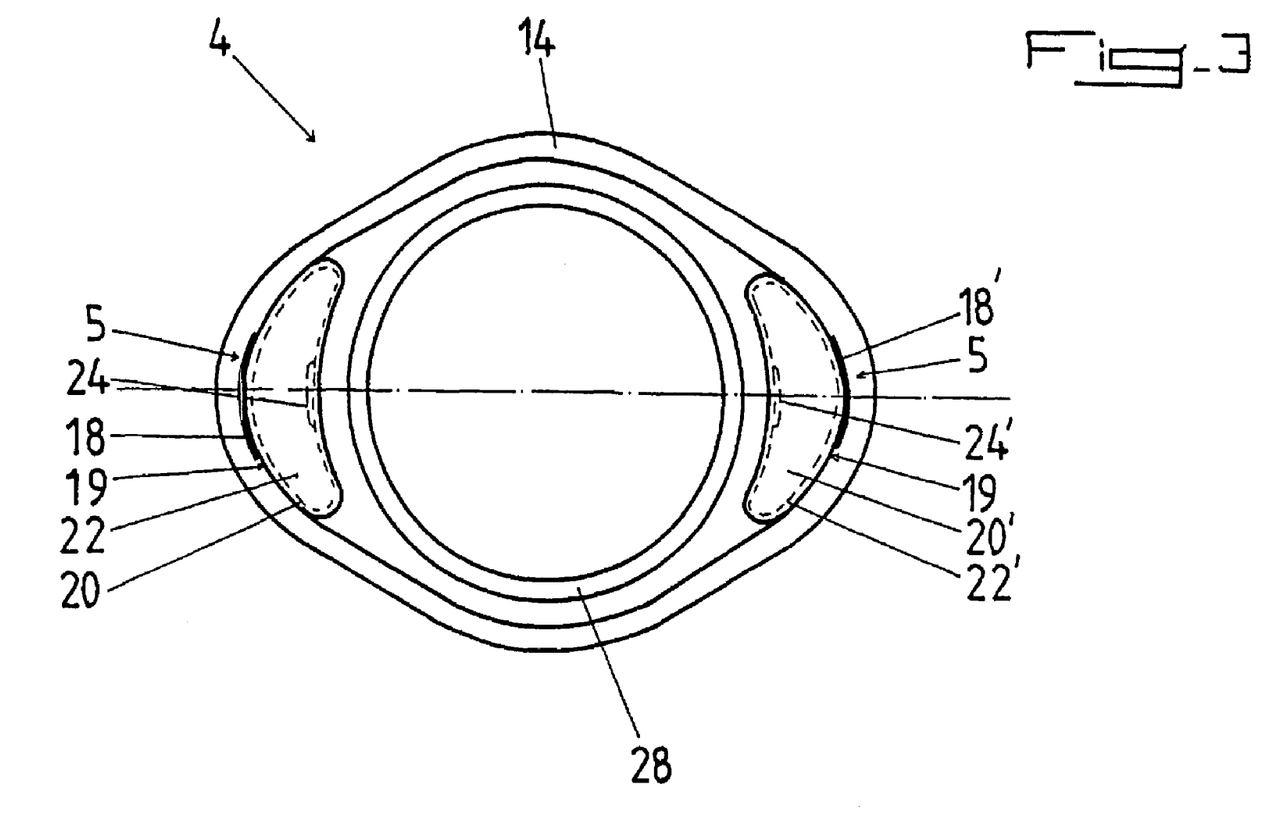
FIG. 3 is a bottom view of the cap of a biological culture growth and observation device according to the present invention.

In a preferred embodiment, and as illustrated on FIGS. 1A and 3, the cap 4 of the devise 1 according to the present invention is designed with cavities or recesses 21, 21' which are bean-shaped and which present means 24, 24' like pads or ribs for improving the grip of the fingers or instruments on the cap 4.

Figures 1, 1B:
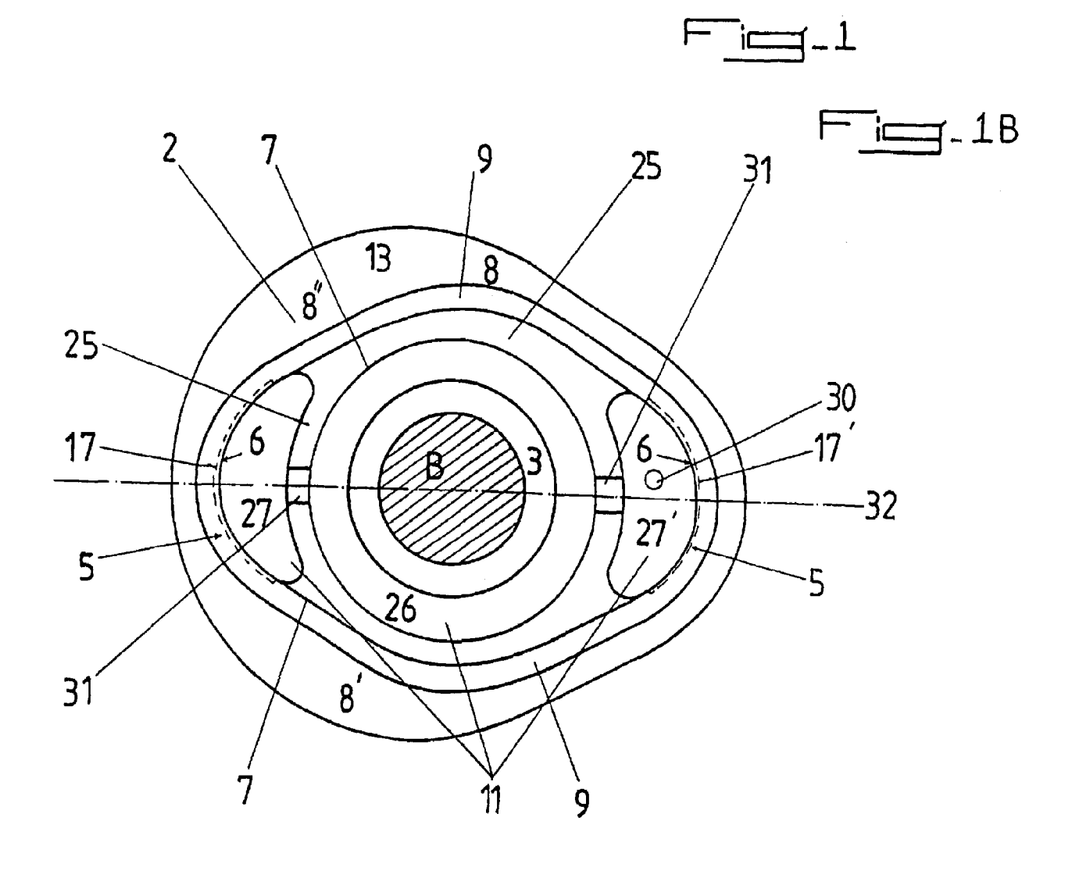
FIG. 1B is a top view of an opened biological culture growth and observation device without seal and cap according to the present invention.

As clearly illustrated on FIG. 1B, the inner volume 11 of the cup-shaped tray 2 is subdivided by one or more inner separation walls or structures 25 to define at least one growth medium 3 containing or receiving chamber 26 and a number of other individually separated chambers 27, 27'.

Like shown said FIG. 1B, the portions of the inner walls 6 of the cup-shaped tray 2 which are provided with first elements 17, 17' of a locking unit 16, 16' to snap the cap on/off said tray 2 are part of the walls defining the chambers 27, 27' which are form-fitted to receive the complementary shaped cavities or recesses 21, 21' located in the cap 4 which form the locking members 20, 20' (not shown here) having the second elements 18, 18' to form with said first elements 17, 17' the engaged locking units 16, 16'.

Figure 6:
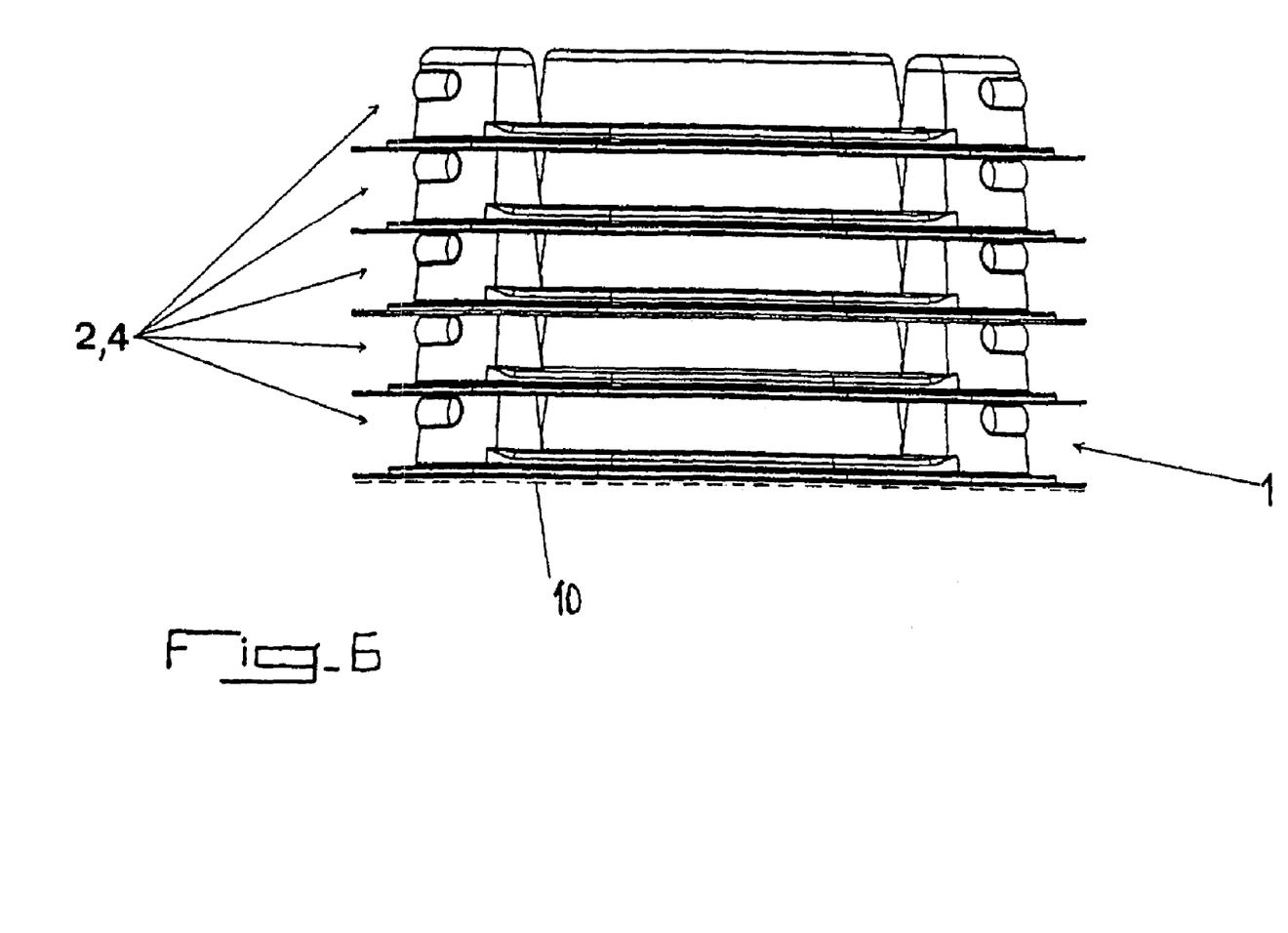
FIG. 6 is a schematic side view of a stack formed of several used or unused devices according to the present invention.

In a particularly interesting version the device 1 is characterized in that the sections 22, 22' and 22", 22''' of the cavities or recesses 21, 21' of cap 4 and the chambers 27, 27' of tray 2 are reducing when moving towards the bottoms 23, 23' and 23", 23''' of said cavities or recesses 21, 21' and said chambers 27, 27' in order to allow for the (with cap 4 covered) trays 2, which removable seals 10 have already been removed, to be stacked as schematically represented on FIG. 6.

In this way, prepared samples of cultures deposited on the growth medium 3 can be stored economically during the growing period in an incubator. The prepared samples can also be transported more easily and need less space when being analysed on the work desk. The space used to store waiting samples contained in the devices 1 or to discard old or useless devices 1 can also be reduced in this manner, which is very advantageous for laboratories where space is rare and expensive.

Device 1 is also characterized in that the growth medium 3 containing or receiving chamber(s) 26 is/are circular and completely separated from the chamber(s) 27, 27' containing the locking members 20, 20' of locking units 16, 16'.

It should be understood that the growth medium 3 containing or receiving chamber(s) 26 can be non-circular (square, triangular, rectangular . . . ), for instance when the device 1 is not used for biological or microbiological uses where isotropic shapes are needed. For medical, biological or similar applications the circular shape is preferred or obligatory, since this shape is the standard shape in these fields and employed for or in numerous normalized tests or equipments devices.

Device 1 according to the present embodiment is characterized in that the cap 4 presents a circular reinforcement ring 28 with a outwardly extending ring-shaped edge 29 on its side which is opposite to the inner volume 11 defined by the tray 2, said ring-shaped edge 29 being aligned with the edges of the wall(s) or structures 25 defining the single central inner circular growth medium 3 containing or receiving chamber 26 (FIGS. 1A and 5).

When turning the cap 4 up-side down, the circular reinforcement ring 28 with a outwardly extending ring-shaped edge 29 can also be used as an annular groove for collecting drops of moisture or of liquid falling from the medium 3 above.

In a special mode of realisation depictured on FIG. 1B, one or more of the chambers 27, 27' which do not contain the growth medium 3 can contain(s) one or several gas developing means 30, for example a $CO_2$ releasing tablet, to create specific growth conditions for the culture contained in said device 1.

This feature makes the device 1 of the invention suitable for the growing of almost any organism, provided the adapted growth medium 3 is used thereby avoiding the multiplication of different kinds of growing devices for different atmospheric conditions.

Of course other gases like air, nitrogen, more or less diluted oxygen, etc. may also be employed by using the right gas-emitting substance or by establishing a proper connection of chamber 26 to an external automatically regulated gas-supply system, for example with a needle injecting a gas via a supplying pipe connected to a main tap.

In order to enable or to enhance the passage of the created/supplied gas to the chamber 26 with the culture, the device 1 can have air or gas passages 31 provided between the growth medium 3 containing or receiving chamber 26, the snapped-on cap 4 and the other chambers 27, 27', especially chambers 27, 27' which contain one or several gas developing means 30.

On FIG. 1B, for example, air or gas passages 31 consist, for instance, of small excavations in the separation wall(s) or structures 25, but other constructions like holes or channels are also possible.

In order to enable the locking units 16, 16' to work properly the device 1 according to the present invention is characterized in that the cup-shaped tray 2 and/or the cap 4 are made of a flexible material, preferably of a flexible and optically transparent plastic with unfogging properties.

Tray 2 and/or cap 4 can be made of various kinds of materials, and especially of a great variety of plastics or glasses. Preferably, the plastic used is thermally formable to permit the thermoforming of the cavities or recesses 21, 21' on the cap 4.

The material used for the tray 2 and/or cap 4 of the present invention as well as the material used for the seal 10 are those common to those skilled in the art and have the necessary properties related to their use in the medical or biological field when concerning their physical and chemical properties. Suitable materials are, for instance, non reactive with the growth medium 3 and are not permeable to oxygen, moisture or liquid water.

The thermoplastic material may, for example, be chosen from a wide range of plastics which are well known in the art, such as cellulose propionate, nylon, polyester, polypropylene, polystyrene, polyurethane, polyethylenterephtalate, ABS, polyethylene and vinyl among others. Other materials like glasses, ceramics, metals are also possible, although sometimes with restrictions.

Preferably, the device 1 according to the present invention has a removable seal 10 made of a hermetic material which is hermetically fixed by gluing, welding or the like to the first surface 13 of the first circumferential edge 8 of the cup-shaped tray 2, said material further being, at least locally, an optically transparent material, preferably an optically transparent plastic film.

The hermetic sealing permits the growth culture 3 to be stored without any damage for a longer time (shelf-life) and maintains the integrity of the device 1 (tray 2 with growing medium 3+cap 4) as long as the device 1 remains closed and unviolated. Suitable material for the removable seal 10 are those commonly designated as <<barrier layers>>.

The removable seal 10 is preferably removed just before the biological or microbiological organism is inoculated to the growth medium 3.

Figure 2:
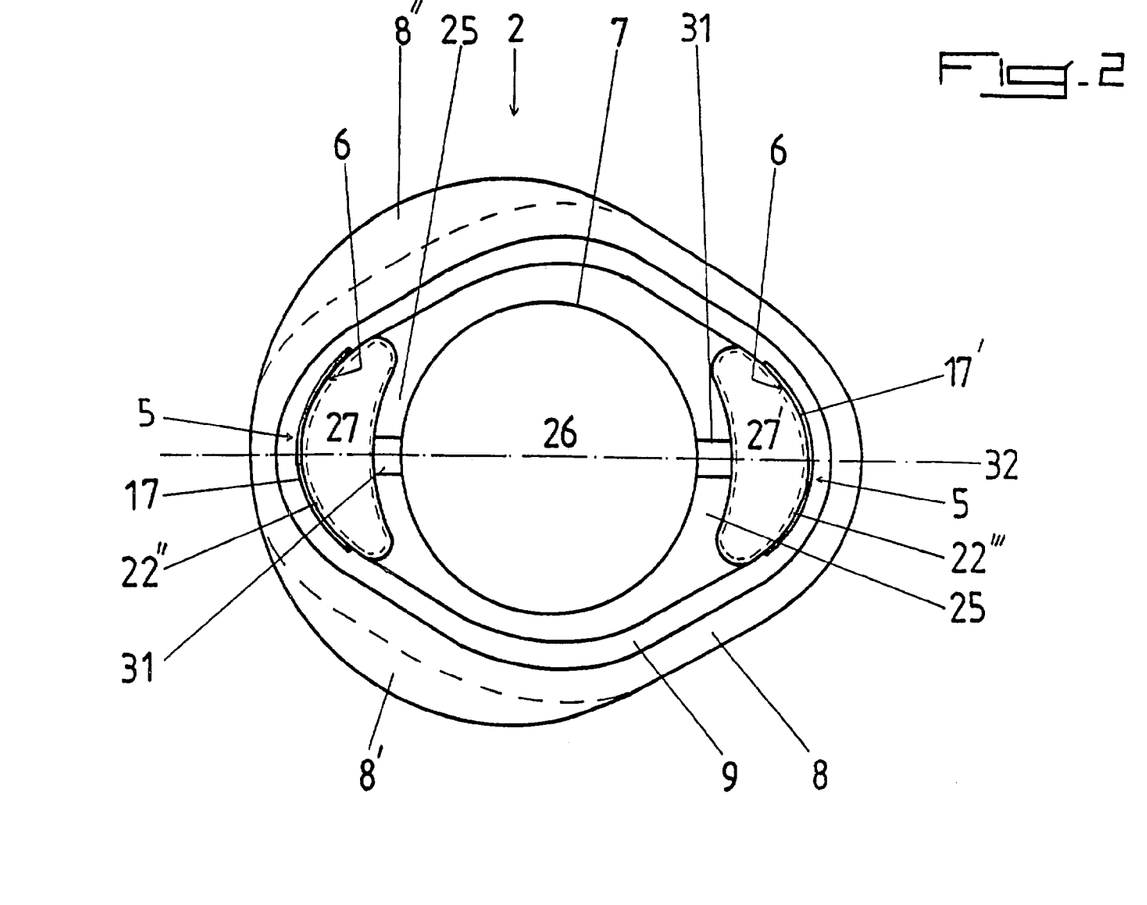
FIG. 2 is a bottom view of the tray of a biological culture growth and observation device according to the present invention.

In the non limitative embodiment represented on FIGS. 1 and 2, the first circumferential edge 8 presents at least one portion 8', 8" with a wider edge to facilitate the peeling of the removable seal 10 before the first use of the device 1 and/or for marking, writing on or labeling the tray on said portion 8'; 8". In order to facilitate the removing of the seal 10 some portions, for example the wider portions 8', 8" of the first surface 13, may not be fixed to the removable seal 10.

In the preferred embodiment illustrated on FIG. 1A, the device 1 has a cup-shaped tray 2 and its cap 4 forming together a stretched device 1 with a longer length and wherein the first circumferential edge 8 has two symmetrically opposite located portions 8', 8" situated on the left and the right side of the length axis 32 of the device 1, said both portions 8', 8" presenting a wider edge to facilitate the peeling of the removable seal 10 before the first use of the device 1 for left or right-handed persons.

The way of using the device 1 according to the present invention can be illustrated in the following example, where a non limitative embodiment of the device 1, as represented on FIG. 1, is used.

The device 1 according to the present invention can be used in mainly two different ways, either with the cap 4 facing the operator or with the cap 4 upside down and oriented towards the surface on which the device 1 is laid.

In the last case, the removable seal 10 has of course to be removed before turning the device 1 upside down and removing the tray 2 upwards.

A first common step in the two general corresponding methods of using the device 1 according the present invention consists in preparing the device 1 by checking a potential contamination through a simple visual test (possible due to the optically transparent material used for the tray 2, the cap 4 and the seal 10) and then peeling of the removable seal 10.

In a more classical first mode, device 1 is then placed on a plane surface with the cap 4 facing the operator. The cap 4 is unlocked from the tray 2 by slightly squeezing it with the fingers of one hand which take off the cap 4 by two cavities or recesses 21, 21' thereby slightly bending the flexible cap 4 which causes the disengaging of the means 5 of the locking units 16, 16'. While said hand is holding the cap 4 instead of laying it down, thereby preventing any contamination of said cap 4, the other hand or an instrument operated by said other hand of the operator can deposit the living organisms or alike onto the growth medium 3 and close the device 1 by simply replacing and pressing delicately the cap 4 on the tray 2 until said cap is snapped on and thus tightly locked to the tray 2. The living organisms may be deposited by any usual method and, for example, especially by depositing a circular membrane containing the biological material (B) to be multiplied or the like in the central growth medium 3 receiving or containing chamber 26, where it stays sticked to said medium 3.

In the second mode, the device 1 is turned upside down and placed on a plane surface with the plane surface 15 of cap 4 resting on said surface. The tray 2 is then unlocked from the cap 4 by slightly squeezing it with the fingers placed on opposite sides of the central chamber 26 thereby slightly bending the flexible tray 2 which causes the engaged means 5 of the locking units 16, 16' to disengage. While the cap 4 remains on the surface, one hand is removing the tray 2 and tilting it so that the growth medium 3 containing or receiving chamber 26 faces the operator, the other hand or an instrument operated by said other hand depositing the living organisms onto the growth medium 3. The device 1 is then closed by turning the tray 2 towards its initial upside down position and by simply pressing it delicately on said cap 4 until said tray 2 is snapped on and thus tightly attached to the cap 4. The living biological material (B) may be as well deposited as a circular membrane containing the cells on the central growth medium 3 receiving or containing chamber 26, where it stays sticked to said medium 3 without any risk of falling down.

A further step common to both ways is then to put the prepared devices 1 up-side down on a stack, among so-prepared other devices 1 (without seal 10) and to put the whole stack in an incubator. During or after the growing period, the device 1 can be removed, observed or treated in any known way.

In this disclosure, there is shown and described only the preferred embodiment of the invention. However, it is to be understood that the invention is capable of use in various other combinations and environments and is capable of changes or modifications within the scope of the invention concept as expressed herein.

The invention claimed is:

1. Biological culture growth and observation device comprising a cup-shaped tray for containing or receiving a growth medium for said biological culture and a cap which matches said tray and which can be snapped on and off said tray, wherein said cap and tray are provided with means to snap on/off said cap on/off inner walls of said tray and in that said cup-shaped tray comprises walls having a first circumferential edge on which a removable seal can be fixed to cover the surface of said first circumferential edge and said cap which is snapped on said tray before the first use of the device, and a second circumferential outwardly extending edge at a lower level than the level of said first circumferential edge, and wherein said cap has a corresponding circumferential outwardly extending edge which is vertically aligned with said second outwardly extending circumferential edge when said cap is snapped on said tray, and wherein said device further comprises at least one locking unit having a first element located on the inner wall of said tray collaborating with at least one second element located on at least one outer surface of at least one locking member extending in a perpendicular or nearly perpendicular direction out of the surface covered by said cap, wherein said cap has two in-molded or in-formed cavities on said covering surface of said cap in such a way that one cavity or recess may receive the thumb of a user's hand whereas the other cavity or recess may receive the index finger and/or another finger of the same hand, thereby allowing said cap to be snapped on/off said tray with only one hand thanks to said at least one locking unit placed at said cavities or recesses, the snapping-off comprising the disengaging of said first and second elements of the locking units, said disengaging being realized by a flexion of the cap and the cup-shaped tray, said flexion moving said first and second elements of said locking units away from each other, said device further comprising a growth medium chamber for containing said growth medium and first and second chambers spaced from one another for receiving respective ones of said two in-molded or in-formed cavities on said covering surface of said cap.

2. Device according to claim 1, wherein said first circumferential edge of said walls of said cup-shaped tray is extending outwards of the inner volume defined by said tray.

3. Device according to claim 2, wherein said first circumferential outwardly extending edge has a first surface, and wherein said corresponding edge of said cap has a second surface, and wherein said first surface and said second surface of said corresponding edge of the cap snapped on said tray are in the same plane or nearly the same plane at nearly the same level.

4. Device according to claim 3, wherein said removable seal is made of a hermetic material which is hermetically fixed by gluing or welding to said first surface of the first circumferential edge of the cup-shaped tray, said material further being an optically transparent material.

5. Device according to claim 1, wherein said cap covering surface is planar or nearly planar.

6. Device according to claim 1, wherein said first and second elements have complementary engaging surfaces which cooperate together to allow the cap to be snapped on/off the cup-shaped tray.

7. Device according to claim 6, wherein said first element and second element of each locking unit comprises a rib/groove collaborating with a corresponding groove/rib having a complementary shape.

8. Device according to claim 6 or 7, wherein there are two locking units on opposite areas of tray and cap to maximize the distance between said locking units.

9. Device according to claim 1, wherein said cavities or recesses are bean-shaped and present means for improving the grip of the fingers or instruments on the cap.

10. Device according to claim 1, wherein the portions of the inner wall of the cup-shaped tray which are provided with said first element of said locking unit to snap the cap on/off said tray are part of the walls defining said first and second chambers which are form-fitted to receive said cavities or recesses located in the cap which form the locking members having the at least one second element to form with said first element the engaged locking units.

11. Device according to claim 10, wherein said cavities have sections and said sections and said first and second chambers of tray are reducing when moving towards the bottoms of said cavities or recesses and said individually separated chambers in order to allow for the trays to be stacked, with said cap covered and said removable seals removed.

12. Device according to claim 10 or 11, wherein said growth medium chamber is circular and completely separated from said first and second chambers containing the locking members of locking units.

13. Device according to claim 12, wherein said cap has a circular reinforcement ring with an outwardly extending ring-shaped edge on its side which is opposite to the inner volume defined by the tray, said ring-shaped edge being aligned with the edges of the wall(s) or structures defining said growth medium containing or receiving chamber.

14. Device according to claim 12, wherein one or more of said first and second chambers do not contain said growth medium and contain(s) one or several gas developing means to create specific growth conditions for the culture contained in said device.

15. Device according to claim 12, further comprising air or gas passages provided between said growth medium containing or receiving chamber, said snapped-on cap and said individually separated chambers.

16. Device according to claim 1, wherein said cup-shaped tray and/or said cap are made of a flexible material comprising optically transparent plastic.

17. Device according to claim 1, wherein said first circumferential edge has at least one portion with a wider edge to facilitate the peeling of said removable seal before the first use of the device and/or for marking, writing on or labeling the tray on said portion of said first circumferential edge.

18. Device according to claim 17, wherein said cup-shaped tray and said cap form together a stretched device with a longer length and wherein said first circumferential edge has two symmetrically opposite located portions situated on the left and the right side of the length axis of the device, said symmetrical portions presenting a wider edge to facilitate the peeling of the removable seal before the first use of the device for left or right-handed persons.

* * * * *